United States Patent
Huwyler et al.

(10) Patent No.: US 7,208,174 B2
(45) Date of Patent: Apr. 24, 2007

(54) LIPOSOME COMPOSITIONS

(75) Inventors: Joerg Huwyler, Burg (CH); Anita Schnyder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/011,266

(22) Filed: Dec. 14, 2004

(65) Prior Publication Data

US 2005/0152963 A1     Jul. 14, 2005

Related U.S. Application Data

(60) Provisional application No. 60/530,881, filed on Dec. 18, 2003.

(51) Int. Cl.
  *A61K 8/14*    (2006.01)
  *C07K 16/00*   (2006.01)

(52) U.S. Cl. ............... 424/450; 530/387.1; 435/7.5

(58) Field of Classification Search ............... 424/450; 530/387.1; 435/7.5
  See application file for complete search history.

(56) References Cited

U.S. PATENT DOCUMENTS

| | | | |
|---|---|---|---|
| 5,527,528 A * | 6/1996 | Allen et al. ............... 424/178.1 |
| 6,139,819 A * | 10/2000 | Unger et al. ............... 424/9.52 |
| 6,210,707 B1 * | 4/2001 | Papahadjopoulos et al. ............... 424/450 |
| 6,803,053 B2 * | 10/2004 | Papahadjopoulos et al. ............... 424/450 |
| 6,852,334 B1 * | 2/2005 | Cullis et al. ............... 424/450 |
| 6,890,556 B1 * | 5/2005 | Segura et al. ............... 424/450 |
| 6,897,196 B1 * | 5/2005 | Szoka et al. ............... 514/1 |
| 6,930,087 B2 * | 8/2005 | Baru et al. ............... 514/2 |
| 6,958,241 B2 * | 10/2005 | Martin et al. ............... 435/458 |

OTHER PUBLICATIONS

Torchilin V P, Biochimica et biophysica acta, (Apr. 2, 2001) 1511 (2) 397-411.*
Laverman P., Journal of nuclear medicine : official publication, Society of Nuclear Medicine, (May 2000) 41 (5) 912-8.*
Biochem J., vol. 377, p. 61-67 (2004), online publication on Sep. 30, 2003.

* cited by examiner

*Primary Examiner*—David Lukton
(74) *Attorney, Agent, or Firm*—George W. Johnston; Dennis P. Tramaloni; Samuel H. Megerditchian

(57) ABSTRACT

The present invention provides a non-covalent coupling method for the preparation of sterically stabilized lipsomes which may be used for targeted drug delivery, e.g., pegylated liposomes. The method simplifies the attachment of targeting vectors to sterically stabilized liposomes. The present invention also provides a liposome composition comprising a compound of the formula

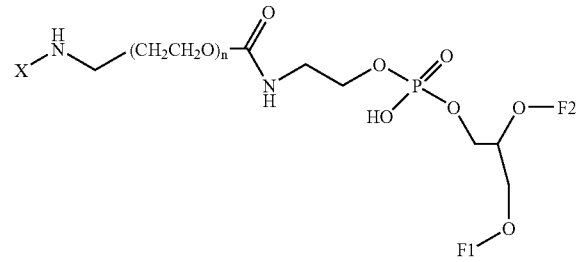

and a compound of the formula Z-Y, wherein Z is any compound capable of binding to a cellular receptor, and X and Y are compounds which can interact with each other non-convalently, and wherein the substituents n, F1 and F2 are as provided in the specification.

15 Claims, 6 Drawing Sheets

LIPOSOME COMPOSITIONS

PRIORITY TO RELATED APPLICATIONS

This application claims the benefit of Provisional Application Ser. No. 60/530,881, filed Dec. 18, 2003.

BACKGROUND OF THE INVENTION

Site-specific delivery of drugs to diseased cells can lead to increased therapeutic effects and to a significant reduction of toxicity. Drug targeting by antibody-conjugated liposomes or immunoliposomes [1] represents a technology which has been applied to the targeting of specific sites of drug action such as the brain [2], lung [3], cancer cells [4–9], HIV-infected cells [10–12] or cells of the immune system [13]. Site specific targeting is mediated by the high affinity binding of monoclonal antibodies, i.e. the targeting vector, to their specific antigens. The efficacy of the method depends thereby, first, on the target specificity of the vector and, second, cellular uptake and intracellular delivery of the liposomal load. In vivo studies have shown that conventional (immuno)liposomes are rapidly removed from the circulation by cells of the reticuloendothelial system, i.e. tissue-resident phagocytes present in a number of organs, particularly the spleen and the liver [17, 18]. This interaction is not observed with sterically stabilized liposomes, which are prepared by insertion of monosialoganglioside (GM1) [19] or poly(ethylene glycol) (PEG) [20] derivatized lipids within the lipid bilayer of conventional liposomes. Such liposomes coated with inert polymers show a substantial improvement in their blood circulation halflife (in human in the order of days as opposed to minutes for conventional liposomes [21]).

Sterically stabilized immunoliposomes are often prepared by coupling of antibodies to the distal ends of PEG chains [2, 5, 22]. Using the PEG chains as linker between the liposome and antibody leads to an enhanced antibody-antigen binding since the antibody is not shielded by the steric barrier activity of PEG. Several covalent coupling methods have been developed for attaching (derivatized) antibodies at the PEG terminus. They make use of functionalized PEG-lipids with a chemically reactive endgroup such as hydrazide, N-(3'-(pyridyldithio)proprionate [23], maleimide [2], succinyl [24], p-nitrophenylcarbonyl [25] or cyanuric chloride [26]. The drawback of these chemical coupling strategies consists in the difficulty to obtain reproducible and high coupling efficiencies [26]. Slow hydrolysis of the reactive PEG-derivative may, for example, compete with antibody binding. This may result in loss of antibody and makes it necessary to determine in separate experiments the amount of bound antibody for each batch of immunoliposomes.

SUMMARY OF THE INVENTION

The present invention provides a liposome composition comprising a compound of the formula

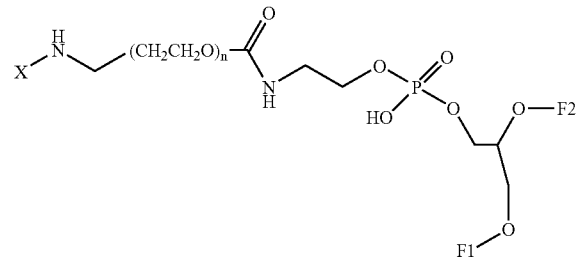

wherein n=from 14 to 85, and F1 and F2 are each independently a fatty acid chain; and
a compound of the formula Z-Y,
wherein Z is any compound capable of binding to a cellular receptor, and X and Y are compounds which interact with each other non-covalently.

The present invention also provides a method for producing a liposome composition comprising
a) conjugating a compound Z with compound Y; and
b) mixing the product of a) with a compound of the formula

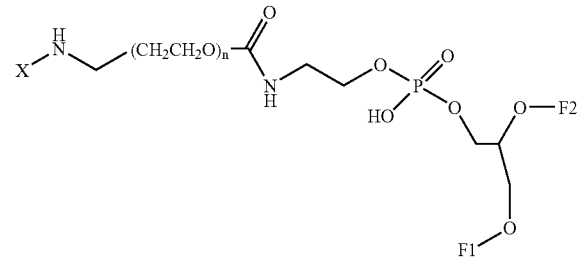

wherein n=from 14 to 85, F1 and F2 are each independently a fatty acid chain, Z is any compound capable of binding to a cellular receptor, and X and Y interact with each other non-covalently.

DETAILED DESCRIPTION OF THE INVENTION

In the present invention, a non-covalent (biotin-streptavidin) coupling procedure for the preparation of pegylated liposome compositions is provided which simplifies the attachment of targeting vectors to sterically stabilized liposomes. As an example, the OX26 murine monoclonal antibody (mAb) to the rat transferrin receptor [14] was used as a vector. However, any receptor ligand, including peptides and small molecules, can be used as a vector for tissue targeting. The OX26 antibody has been shown to bind to an extracellular epitope on the receptor, at a site removed from the transferrin binding site [15]. In cultured cells such as the RG2 rat glioma cell line, receptor mediated endocytosis and thus intracellular accumulation of the OX26 mAb as well as OX26 conjugated liposomes was observed [16].

The present invention provides a new coupling procedure for the preparation of pegylated immunoliposomes. A biotinylated PEG-phospholipid (bio-PEG-DSPE) was used for a non-covalent (biotin-streptavidin) method of attachment of a mAb to sterically stabilized liposomes. The biotin is thereby coupled at the PEG terminus which allows an optimal target recognition of the bound mAb. Coupling of a streptavidin-conjugated antibody is simple, rapid and highly reproducible. Preferably, streptavidin conjugated mAb was used. Such immunoliposomes were found to exhibit reduced non-specific binding and reduced systemic clearance in vivo [28].

Figure 1:
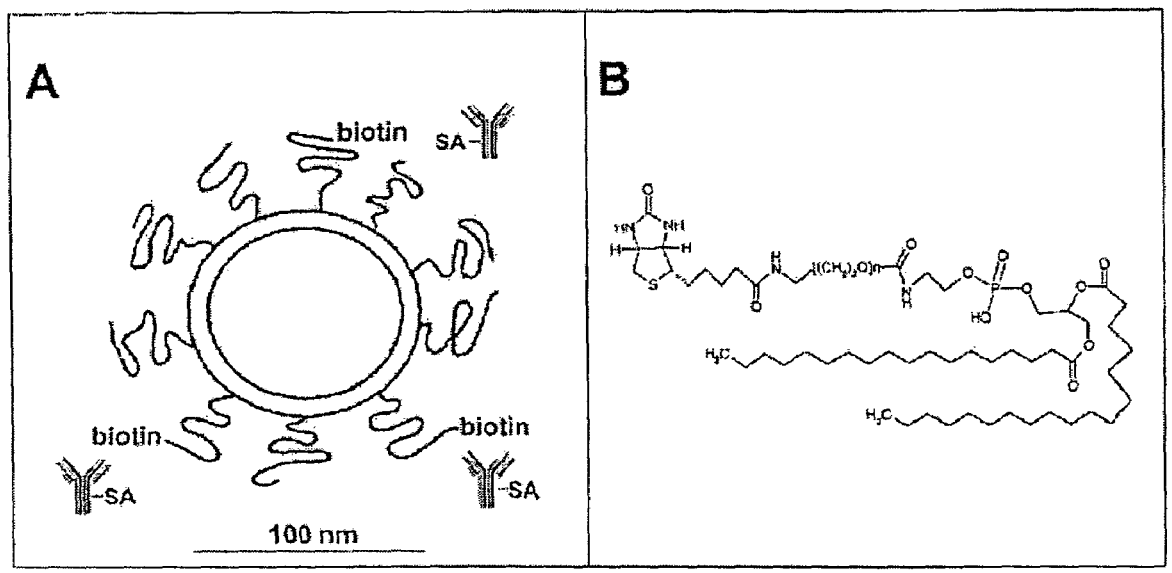
FIG. 1: A: OX26-immunoliposomes are prepared by coupling of streptavidin conjugated OX26 monoclonal antibodies to biotinylated PEG-liposomes. There are approximately 5500 strands of polyethlyene glycol of 2000 Da molecular mass attached to the liposome surface of which approximately 30 carry a biotin group at their distal end. B: Chemical structure of bio-PEG-DSPE, the biotinylated linker phospholipid.

The present invention provides biotinylated immunoliposomes, wherein a streptavidin-conjugated targeting vector (i.e. the OX26 monoclonal antibody to the rat transferrin receptor) is attached to the surface of the liposome using a polyethyleneglycol (PEG) spacer (FIG. 1A). Biotin was thereby coupled to the tip of the pegylated phospholipid PEG-DSPE (FIG. 1B) and subsequently incorporated in sterically stabilized liposomes (PEG-liposomes). A biotinylated PEG-liposome carries approximately 5500 strands of 2000 Da PEG and 30 strands of the linker lipid biotin-PEG-DSPE and has a measured particulate size of 150 nm. The use of PEG as a flexible tether allows the biotin and thereby the attached mAb to extend away from the liposome surface which minimizes steric hindrance by unconjugated PEG moieties.

Previous studies [34] have indeed demonstrated that biotinylation of PEG-lipsosomes does not affect their in vivo pharmacokinetics in control rats but promotes their accumulation in subcutaneous *Staphylococcus aureus* abscesses in the rabbit. Furthermore, direct measurement of the ligand-receptor interaction potential using biotinylated PEG liposomes and streptavidin on a supported lipid bilayer indicated a markedly extended range of the interaction [35].

Thus, the present invention provides a liposome composition comprising a compound of the formula

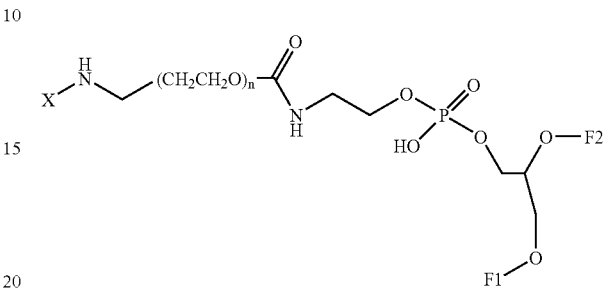

wherein n=14 to 85 and F1 and F2 are each any synthetic or natural fatty acid chain; and a compound of the formula Z-Y, wherein Z is any compound capable of binding to a cellular receptor, and X and Y are compounds which are capable of interacting with each other non-covalently. Preferably, X is biotin and Y is avidin or streptavidin. More preferably, X is biotin and Y is streptavidin.

In a preferred embodiment, n=28 to 50. In another preferred embodiment, F1 and F2 are stearic acid.

Z may be a polypeptide ligand for a cellular receptor, or a compound capable of binding to a cellular receptor [42]. In a further preferred embodiment, Z is an antibody. In this embodiment, the liposome composition is an immunoliposome composition. In a most preferred embodiment, Z is an OX26 monoclonal antibody. Targeting vectors may also be produced as recombinant fusion proteins, e.g. a streptavidin fusion protein [36].

Biotinylated PEG-liposomes can be used for the non-covalent conjugation of any avidin- or streptavidin-conjugated ligand. Such ligands could, for example, include genetically engineered single chain antibody-streptavidin fusion proteins, such as the OX26 single chain Fv antibody-streptavidin fusion protein [36], which can be produced on large scale in procaryotic or eucaryotic expression systems [37].

In a preferred embodiment, the monoclonal antibody was an anti-transferrin-receptor antibody. In a more preferred embodiment, the monoclonal antibody is the OX26 anti-transferrin antibody. The transferrin receptor mediates endocytosis of iron bound to the plasma glycoprotein transferrin. Transferrin receptors are expressed by a variety of cells but their expression levels vary greatly [29]. As a consequence, receptor mapping studies using different antibodies to the human transferrin receptor have demonstrated binding to different organs and tissues in cynomolgus monkeys [30]. Interestingly, skeletal muscle was among tissues from which the highest percentages of the injected doses of antibody were recovered [30]. We therefore decided to explore if the OX26 mAb to the rat transferring receptor would bind to rat skeletal muscle and if this antibody could subsequently serve as a targeting vector in a novel design of biotinlylated immunoliposomes.

The present invention pertains to a method of producing a liposome composition comprising conjugating a compound Z with compound Y, and mixing the product of a) with a compound of the formula

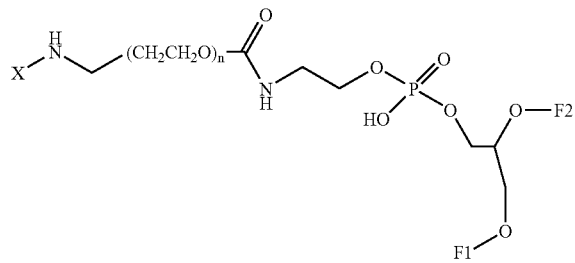

wherein n=14 to 85 and F1 and F2 are any synthetic or natural fatty acid chain, wherein Z is any compound capable of binding to a cellular receptor, and wherein X and Y interact with each other non-covalently. In one preferred embodiment, X is biotin and Y is avidin or streptavidin. In a more preferred embodiment X is biotin and Y is streptavidin. In another preferred embodiment, n=28 to 50. In a further preferred embodiment, F1 and F2 are stearic acid.

Z may be a polypeptide ligand for a cellular receptor, or a compound capable of binding to a cellular receptor. In a further preferred embodiment, Z is an antibody. In a most preferred embodiment, Z is an OX26 monoclonal antibody.

Figure 4:
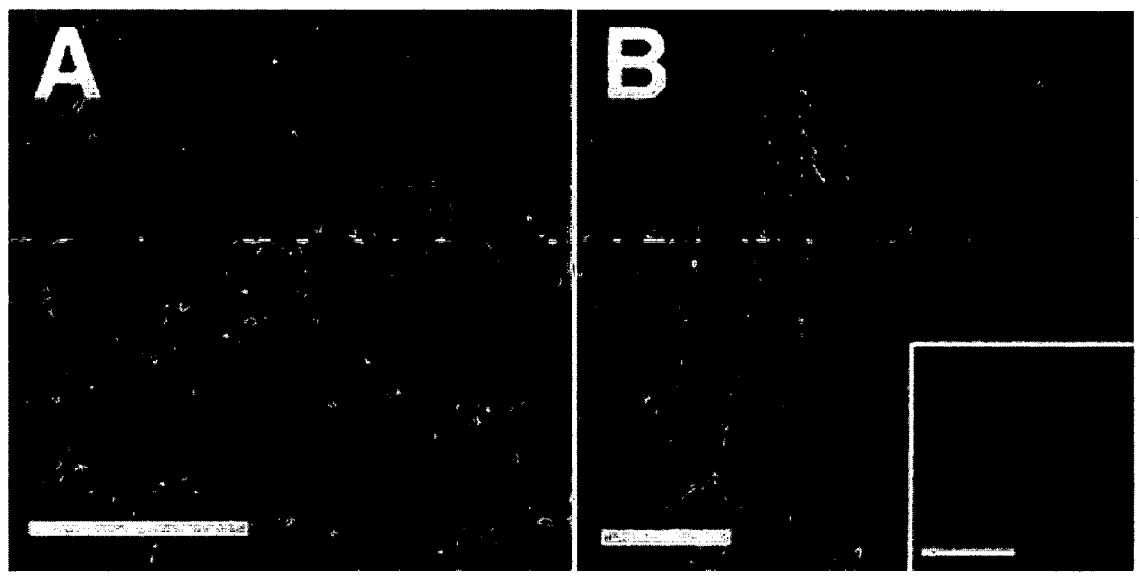
FIG. 4: Analysis of muscle tissue sections by confocal microscopy using the OX26 mAb (125 µg/ml) and a secondary Cy2 labeled polyclonal antibody. Immunostaining of rat muscle tissue which is cryo sectioned A: orthogonal or B: parallel to the muscle fibers. Inset: control, incubation with secondary antibody only. Size bars=100 µm.

The question arises if targeting of skeletal muscle could be achieved using OX26-SA as a vector directed against the transferrin receptor. The transferrin receptor is expressed by different organs such as the liver, spleen, general vascular endothelium and the blood brain barrier. In skeletal muscle, transferrin has been shown to play an important role in muscle growth, i.e. the process of myoblast and satellite cell proliferation, their fusion to myotubes and their further differentiation to muscle fibers [39]. Studies with, for example, primary cultures of chick muscle cells [40] have clearly demonstrated high expression levels of functional transferrin receptors regardless of the state of growth or differentiation of these cells. We confirm by immunostaining experiments using the OX26 monoclonal antibody the presence of the transferrin receptor in rat skeletal muscle tissue (FIG. 4). Tissue sections perpendicular to the muscle fibers (FIG. 4a) show an intense immunostaining at the periphery of myofibers (which have a diameter of 50 to 100 µm) as well as at the periphery of the enclosed myofibrils. The staining of the myofiber surface can also be seen in longitudinal sections (FIG. 4b). Little or no fluorescent signal was observed in control experiments using secondary antibody only (FIG. 4b, inset) or an unspecific mouse $IgG_{2a}$ isotype control antibody (data not shown). Incubation of L6 cells, a cell line derived from rat skeletal muscle, with OX26 mAb at 37° C. followed by visualization of the OX26 mAb using a fluorescent secondary antibody (FIGS. 5a and 5b) reveals fluorescent signal on the cell surface as well as a particulate intracellular staining pattern. This observation suggests that the OX26 mAb is internalized by L6 cells under cell culture conditions and subsequently accumulates within the endosomal compartment of these cells. At 4° C., binding of OX26 to the cell surface only was observed (FIG. 5c) due to inhibition of receptor mediated endocytosis at low temperature. Our findings are in line with previous reports on expression levels of the transferrin receptor in L6 cells which indicated a receptor density of approximately 200'000 receptors per L6 myocyte [41]. We conclude from these experiments that the L6 cell line can be considered to be a representative cell culture model of skeletal muscle which may be used to study transferrin-receptor mediated transport processes in vitro. Uptake experiments in L6 cells (FIG. 6) demonstrated that the functionality of the OX26 mAb is retained after chemical modification and coupling to SA. Incubation of OX26-SA, which was fluorescence labeled using biotin-fluorescein, resulted in a strong intracellular accumulation of fluorescence in L6 cells (FIG. 6a).

Similar results were obtained using carboxyfluorescein-loaded OX26-immunoliposomes (FIG. 6b). The observed effects were mediated specifically by the OX26 mAb since competitive inhibition of cellular uptake was observed in presence of free OX26 mAb (FIG. 6c).

The percentage of positive cells in these experiments was estimated to be over 90%. We conclude that biotinylated OX26-immunoliposomes, despite their big particulate size of 150 nm, are transported across the plasma membrane of L6 muscle cells by means of receptor-mediated endocytosis.

In the present invention, a novel design of biotinylated immunoliposomes was developed and validated. Using the streptavidin-conjugated OX26 mAb directed against the rat transferrin receptor, targeting of immunoliposomes to L6 skeletal muscle cells in vitro followed by intracellular accumulation was achieved. The question arises if such an immunoliposome design could be used for drug targeting to skeletal muscle in vivo. Previous studies demonstrated that a similar design of immunoliposomes had favorable in vivo pharmacokinetic properties such as minimal unspecific tissue binding [2, 16]. Tissue distribution of the immunoliposomes was mediated by the OX26 mAb with selective accumulation in brain tissue. However, receptor mapping studies in cynomolgous monkey using monoclonal antibodies against the human transferrin receptor showed that distribution of such antibodies was not confined to brain tissue but that a significant percentage of the injected dose did accumulate in other tissues expressing the transferring receptor such as skeletal muscle [30]. Interestingly, the over-all pattern of tissue distribution was quite different for the two monoclonal antibodies which were tested. This may be a consequence of binding of the antibodies to different structural motives on the transferrin receptor. These results together with our findings suggest that in vivo drug targeting to skeletal muscle may be achieved by targeting of the transferrin receptor. The tissue specificity will thereby depend on the used anti-transferrin receptor antibody. Biotinylated PEG-liposomes in combination with a streptavidin-conjugated vector to the transferrin receptor are thus a versatile platform to refine in vivo an immunoliposome based delivery system for targeting of drugs to skeletal muscle.

The present invention also pertains to a use of a compound of the formula

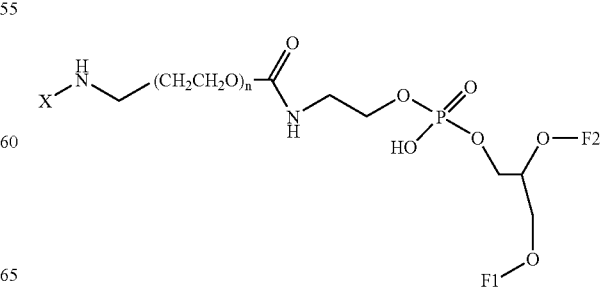

wherein n=14 to 85, and F1 and F2 are any synthetic or natural fatty acid chain; and of a compound of the formula Z-Y for the production of immunoliposomes, wherein Z is any compound capable of binding to a cellular receptor and wherein X and Y interact with each other non-covalently. In one preferred embodiment, X is biotin and Y is avidin or streptavidin. In a more preferred embodiment X is biotin and Y is streptavidin. In another preferred embodiment, n=28 to 50. In a further preferred embodiment, F1 and F2 are stearic acid.

Z may be a polypeptide ligand for a cellular receptor, or a compound capable of binding to a cellular receptor. In a further preferred embodiment, Z is an antibody. In a most preferred embodiment, Z is an OX26 monoclonal antibody.

More preferred is an immunoliposome of the formula

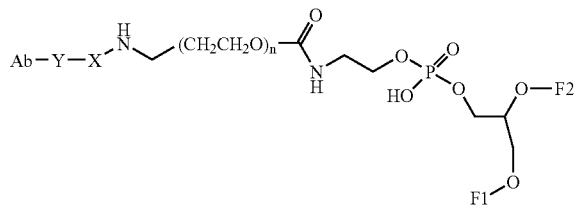

wherein n=from 14 to 85, F1 and F2 are each independently a fatty acid chain, Ab is an antibody capable of binding to a cellular receptor antigen, and X and Y are compounds which are non-covalently bound to each other.

Preferably, X is biotin and Y is avidin or streptavidin.

EXAMPLES

Materials

Cholesterol and Distearoylphosphatidylcholine (DSPC) were from Sigma (St. Louis, Mich.). Pegylated distearoylphosphatidylethanolamine (PEG-DSPE) was purchased from Avanti Polar Lipids (Alabaster, Ala.). For conjugation of the OX26 mAb to the liposome, a biotin-derivatized linker lipid was used which consists of a bifunctional 2000-Da polyethylene-glycol (PEG) that contains a lipid on one end (distearoylphosphatidylethanolamine (DSPE)) and a biotin molecule at the other end.

Biotinylated PEG-DSPE (bio-PEG-DSPE) was custom synthesized by Shearwater Polymers (Huntsville, Ala.). 5(6)-Carboxyfluorescein was purchased from Acros Organics (Geel, Belgium), Sephadex G-75 and Sephacryl S-200 High Resolution were from Amersham Pharmacia Biotech (Uppsala, Sweden). Cy2-conjugated secondary antibody was from Jackson Laboratories (West Grove, Pa.). Unspecific mouse $IgG_{2a}$ isotype monoclonal antibody was from Sigma. [31]Biotin was from Amersham Pharmacia Biotech. The $IgG_{2a}$ anti-rat transferrin receptor OX26 monoclonal antibody (MRC OX-26) [14] was harvested from cell culture supernatants of the OX26 hybridoma cell line and was purified by protein G Sepharose affinity chromatography as described [28]. The OX26 mAb was thiolated using 2-iminothiolane (Traut's reagent) (Sigma) as described previously [2] by conversion of one primary amine per mAb and then linked to streptavidin (Sigma) by activation of the latter with m-maleimidobenzoyl Nhydroxysuccinimide ester (MBS) (Pierce, Rockford, Ill.). All other chemicals were of analytical grade and were obtained from commercial sources.

Streptavidin-Conjugated mAb

Synthesis of Streptavidin-Conjugated OX26 mAb

Figure 2:
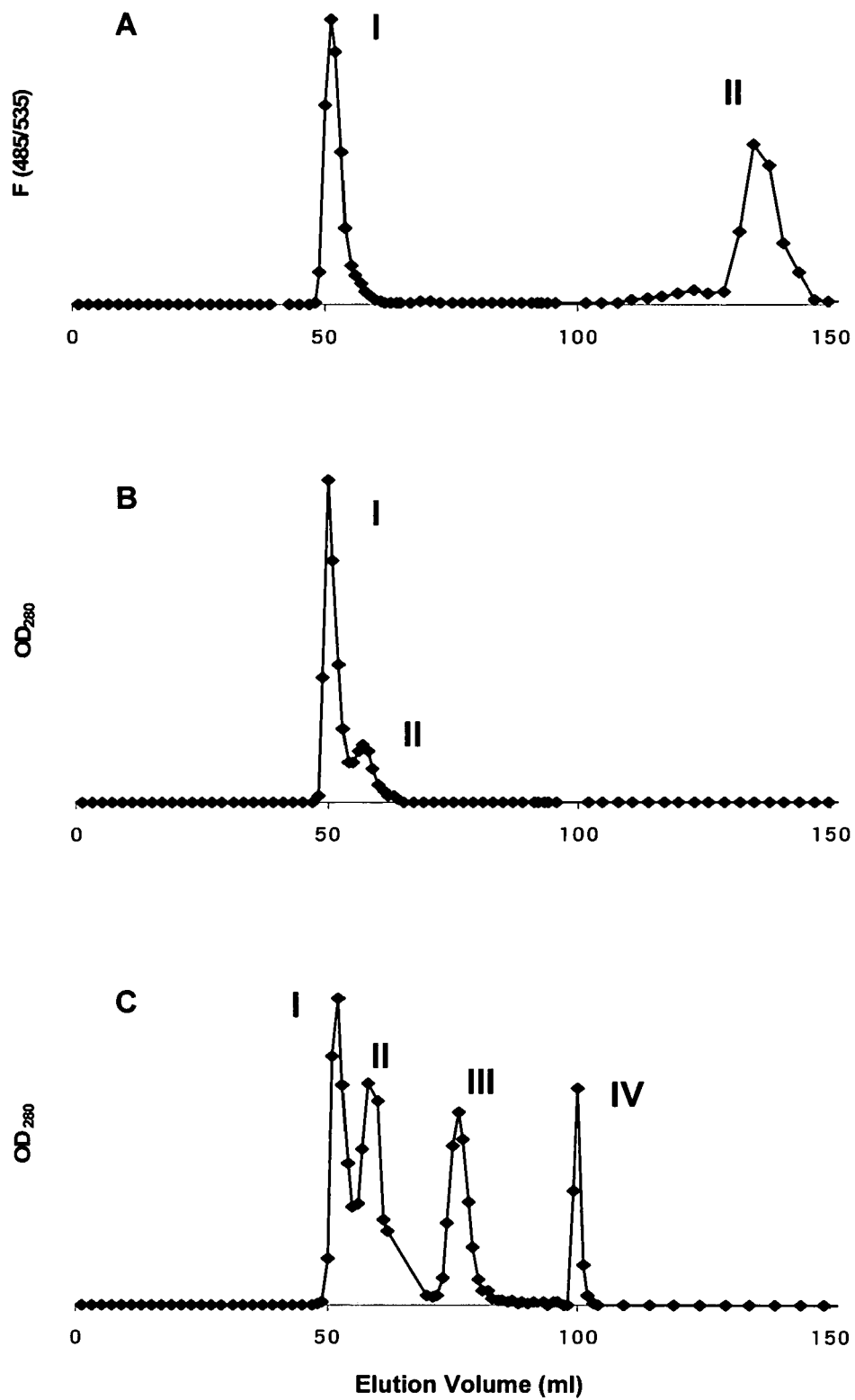
FIG. 2: Column chromatography separation and analysis of OX26-SA using a Sephacryl S-200 packed column. A: Elution profile by fluorescence detection of OX26-SA (I) labeled with an excess of fluorescein-labeled biotin (II). B: Chromatographic separation after synthesis of OX26-SA (210 kDa; I) and unconjugated OX26 (150 kDa; II). C: Elution profile of a set of molecular weight markers: Thyroglobulin of 670 kDa (void volume, I), gamma-globulin of 158 kDa (II), ovalbumin of 44 kD (III), myoglobin of 17 kDa (IV) and vitamin B12 of 1.35 kDa (V).

Streptavidin was chemically combined with the hybridoma generated OX26 monoclonal antibody (mAb). MBS (m-maleimidobenzoyl-N-hydroxysuccinimide ester) was used as a heterobifunctional cross-linker reactive for primary amines in streptavidin and a single sulfhydryl group introduced into the OX26 mAb by thiolation with Traut's reagent (2-iminothiolane). This procedure has been shown previously to retain both the antigen affinity of the OX26 mAb [2] as well as the biotin binding site of streptavidin [38]. The OX26-SA conjugate was purified and analyzed by gel filtration chromatography (FIG. 2).

The OX26 mAb (1.65 mg, 11.2 nmol) was thiolated by using a 20:1 molar excess of 2-iminothiolane (Traut's Reagent) as described previously [2]. By this procedure a single thiol reactive group is introduced into the OX26 mAb. In parallel with the antibody thiolation, streptavidin (SA) (2 mg, 33 nmol) was dissolved in 200 µl 0.1 M PBS (100 mM phosphate, 150 mM sodium chloride, pH 7.4) and activated by using a 20:1 molar excess of m-maleimidobenzoyl-N-hydroxysuccinimide ester (MBS, Pierce, Rockford, Ill.) [27]. After incubation for 1 h at room temperature with gentle shaking, the reaction mix was purified by Sephadex G-75 gel filtration chromatography and UV detection at 280 nm. The thiolated antibody was conjugated to the activated streptavidin at a molar ratio of 1:3 (OX26:SA) by incubation over night at room temperature and gentle shaking. The reaction products were purified by Sephacryl S-200 gel filtration chromatography and OX26-SA containing samples were detected by absorbance measurements at 280 nm. The protein concentration was quantified by the Pierce BCA Protein Assay (Pierce, Rockford, Ill.) using bovine serum albumin (BSA) as reference. OX26-SA was stored in 0.01 M PBS (10 mM phosphate, 150 mM sodium chloride, pH 7.4) at −20° C.

Biotin Binding Assay

Figure 3:
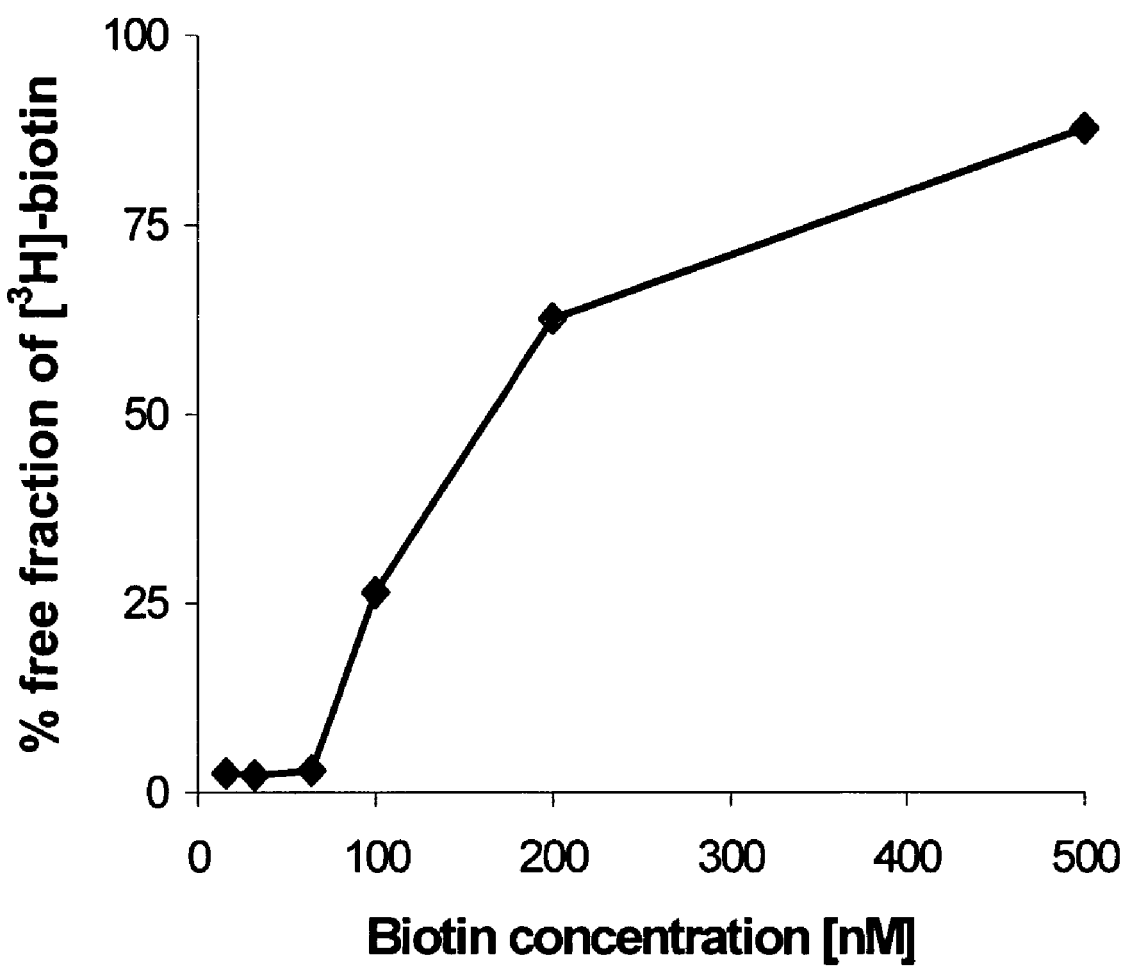
FIG. 3: Concentration-dependent binding of [$^3$H]biotin to a streptavidin-OX26 conjugate. Unbound [$^3$H]biotin was separated from SA-OX26 by ultrafiltration using a filter membrane with a molecular weight cut-off of 30 kDa. Saturation of total [$^3$H]biotin binding in presence of 32 nM of streptavidin-OX26 was observed at biotin concentrations of 64 to 100 nM.

Binding of [24]biotin to the neutral streptavidin-OX26 conjugate was determined by an ultrafiltration method using Centrifree. MPS micropartition devices (Millipore, Bedford, Mass.) containing a low-adsorptive hydrophilic membrane with a 30 kDa exclusion. The binding measurements were performed in a final volume of 1 ml of 10 mM PBS containing 0.1 µCi of [24]biotin and unlabeled biotin at concentrations ranging from 16 to 500 nM. The assay was initiated by the addition of neutral streptavidin-OX26 to a final concentration of 32 nM. Samples were incubated for 15 min at 37° C. and unbound biotin was separated from the bound fraction by centrifugation (for 10 min at 1250×g followed by 2 wash steps). The percentage of unbound biotin in the filtrates were determined by liquid scintillation counting (Packard beta counter, Downers Grove, Ill.). The conjugate was identified by a shift in molecular weight, as compared to unconjugated OX26 mAb, and its ability to bind the fluorescent label biotin-fluorescein (FIG. 2a). A separation was achieved between cross-linked precipitates, OX26-SA (FIG. 2b, peak I) and unbound OX26 mAb (FIG. 2b, peak II) and confirmed by SDSPAGE analysis (data not shown). The approximate yield of SA-conjugated OX26 recovered after purification was 40%. The binding capacity of the OX26-SA conjugate for [24] biotin was determined by an ultrafiltration method (FIG. 3). There are normally four biotin binding sites on the tetrameric streptavidin [27]. Analysis of the biotin binding curve indicates that biotin binding is only partially impaired as a consequence of the coupling of SA to the OX26 mAb. Due to the extremely high affinity of biotin to streptavidin with a $K_D$ approximating $10^{-15}$ M [27], the affinity constant of the OX26-SA conjugate per se can not be determined. However, using 32 nM of the OX26-SA conjugate, saturation of biotin binding is observed between 64 nM and 100 nM biotin indicating the presence of 2 to 3 biotin binding sites on each OX26-SA conjugate. The presence of multiple biotin binding sites on each OX26-SA conjugate may potentially lead to crosslinking of biotinylated liposomes and thus to the formation of liposomal aggregates. To minimize this risk and to block excess biotin binding sites, free biotin was added to OX26-SA in a molar ratio of 1:1 prior to coupling of the OX26-SA conjugate to biotinylated liposomes.

Preparation of Fluorescencent Biotinylated OX26-Immunoliposomes

DSPC (5.2 µmol), cholesterol (4.5 µmol), PEG-DSPE (0.3 µmol) and linker lipid (bio-PEG-DSPE, 0.015 µmol) were dissolved in chloroform. A lipid film was prepared by vacuum evaporation using a Rotavapor (Büchi, Switzerland). Dried lipid films were hydrated at 40° C. in 0.01 M PBS, such that a final lipid concentration of 10 mM was achieved. For the preparation of carboxyfluorescein filled immunoliposomes, the dried lipids were hydrated in 0.01 M PBS containing 0.1 mM 5(6)-carboxyfluorescein. Lipids were subjected to 5 freeze-thaw cycles followed by extrusion (5 times) at room temperature through a 100 nm pore-size polycarbonate membrane employing an extruder (Avestin, Ottawa, Canada). Extrusion was repeated 9 times using a 50 nm polycarbonate membrane. Mean vesicle diameters were 150 nm as determined by dynamic light scattering using a Zetasizer 4 Particle Analyzer (Malvern Instruments, Worcestershire, UK).

Buffer was exchanged for 10 mM PBS by applying the liposome suspension to a 1.6×20 cm Sephadex G-75 column. Aliquots of column eluates were analyzed by on-line absorbance measurements at 280 nm. Fractions containing fluorescent biotin-liposomes were used immediately for conjugation with streptavidin linked OX26 mAb by addition of antibody (bio-PEG-DSPE:OX26-SA=1:1, molar ratio). Excess biotin binding sites on the OX26-SA vector were blocked prior to coupling to the biotinylated liposomes using free biotin (OX26-SA:biotin=1:1, molar ratio) in order to minimize crosslinking and thus precipitation of immunoliposomes. The average number of biotin-PEG-DSPE and thus bound mAb per liposome was calculated to be 30 assuming that one 100 nm liposome contains 100'000 phospholipid molecules [23].

Immunohistochemistry

For immunohistochemistry of skeletal rat muscle tissue, fresh rat muscle tissue fragments were transferred to plastic moulds (Tissue-Tek Cryomould, Miles, Torrance, Calif.), embedded in Tissue-Tek OCT reagent and were frozen immediately in a mixture of isopropanol and dry ice. Samples were kept at −70° C. until use. Sections (6 µm) of the frozen OCT-embedded tissue samples were made using a HM560 cryostat (Microm, Volketswil, Switzerland), mounted on uncoated coverslips, dried for 24 hours at room temperature, fixed with ice-cold 4% paraformaldehyde for 20 min and washed with PBS. All subsequent incubations were done using PBS containing 3% fetal calf serum (FCS) to reduce unspecific binding. Sections were incubated with mAb OX26 (125 µg/ml) for 30 min at room temperature, washed with PBS containing 3% FCS and incubated with rabbit Cy2 secondary anti-mouse antibody (Jackson Laboratories) for 1 hour (1:200 dilutions of antibody). Fluorophor protector (FluorSafe Reagent, Calbiochem, San Diego, Calif.) was added to the sections, slides were sealed and analyzed by confocal microscopy using a Zeiss LSM 510 confocal microscope. Control experiments done in parallel did include incubations with secondary antibody only. Alternatively, the primary OX26 mAb was substituted by an unspecific mouse monoclonal $IgG_{2a}$ isotype control antibody.

Immunocytochemistry and Uptake

Early passages of L6-cells (ATCC catalog No. CRL-1458) [32] were obtained from ATCC (Manassas, Va.) and were grown using DMEM supplemented with 4 mM Lglutamine, 1.0 mM sodium pyruvate, 4.5 g/L glucose, 1.5 g/L sodium bicarbonate, 10% heat-inactivated fetal calf serum (FCS), 100 µg/ml streptomycin and 100 units/ml mpenicillin G (all Gibco-BRL, Paisley, Scotland).

Cell surface expression of the transferrin receptor as well as intracellular accumulation of the OX26 mAb by L6 cells was visualized by immunostaining experiments: L6 cells were grown on chamber slides (Nalge Nunc, Naperville, Ill.). In order to visualize surface expression of the transferrin receptor, L6 cells were incubated on ice for 30 min with the OX26 mAb (100 µg/ml). Cellular uptake and intracellular accumulation of the OX26 mAb was visualized by incubations for 30 min at 37° C. under cell culture conditions with OX26 mAb (30 µg/ml). Cells were washed and fixed for 20 min with ice-cold 4% paraformaldehyde, permeabilized by incubation for 5 min at room temperature with 0.5% Triton X100 in PBS, transferred for 15 min at room temperature to PBS containing 3% FCS and incubated with rabbit Cy2 secondary anti-mouse antibody (Jackson Laboratories) for 1 hour [33]. All incubations with antibody were done using PBS containing 3% fetal calf serum (FCS) to reduce unspecific binding. Cells were mounted in Fluor-Safe Reagent (Calbiochem, San Diego, Calif.) and analyzed by confocal microscopy (Leica TCS NT confocal microscope). Control experiments done in parallel did include incubations with secondary antibody only or the use of an unspecific mouse monoclonal $IgG_{2a}$ isotype control antibody.

Uptake experiments with OX26-conjugates (i.e. OX26 conjugated to streptavidin or OX26 immunoliposomes) were performed with L6 cells grown on chamber slides (Nalge Nunc). Fluorescent OX26-immunoliposomes (carrying 70 µg/ml of bound OX26 mAb) or biotin-fluorescein bound to OX26-SA (70 µg/ml) in 10 mM PBS were diluted with one volume of cell culture medium. Incubations with L6 cells were done for 1 hour at 37° C. Competition experiments were done in presence of 200 µg/ml of OX26 after 15 min pre-incubation of the cells with the free OX26. Cells were washed four times with ice-cold 10 mM PBS and fixed (20 min at 4° C.) using 200 µl of 4% paraformaldehyde. Cells were washed and mounted using FluorSafe Reagent (Calbiochem). Slides were sealed and analyzed by confocal fluorescence microscopy (Leica TCS NT confocal microscope).

Microscopy

Figure 5:
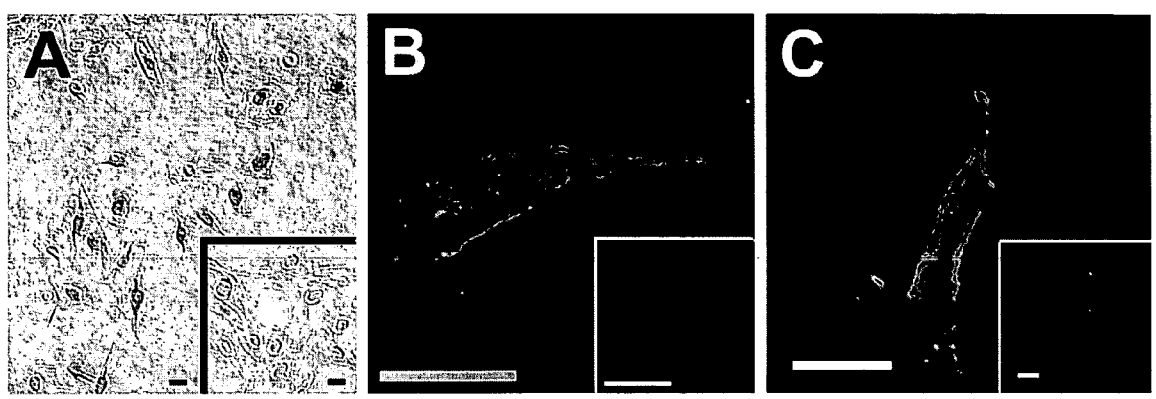
FIG. 5: Immunocytochemistry and uptake experiments using the OX26 mAb and L6 cells. A: Cellular uptake of the OX26 mAb (100 µg/ml) by L6 cells at 37° C. and visualization of internalized antibody using a Cy2 labeled secondary antibody: Overlay between a phase contrast image of L6 cells and the corresponding fluorescence image. Inset: negative control using an unspecific IgG$_{2a}$ isotype antibody. B: Magnification of a single L6 cell (incubation with 30 μg/ml of OX26 at 37° C.) reveals a particulate intracellular staining pattern. Inset: control, secondary antibody only. C: Immunolabeling of surface receptors by incubation of L6 cells with OX26 mAb (100 μg/ml) at 4° C. Inset: control, unspecific IgG$_{2a}$ isotype antibody. Size bars =20 μm.
Figure 6:
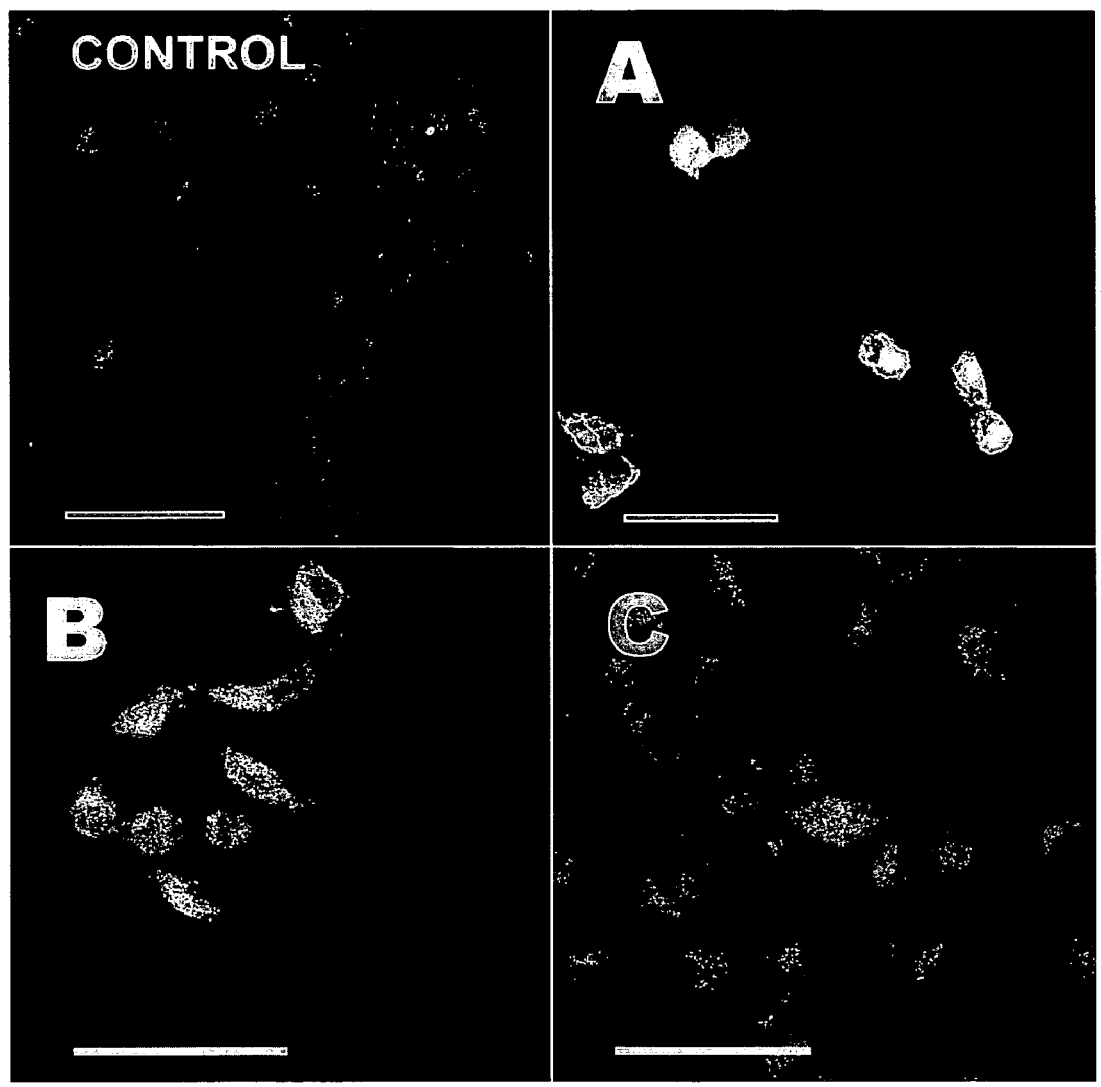
FIG. 6: Cellular uptake of fluorescence labeled OX26-streptavidin (OX26-SA-biotinfluorescein) and fluorescent OX26 immunoliposomes by cultured L6 muscle cells. Cells were fixed after one hour incubation and analyzed by confocal microscopy. Concentration of OX26 was always 70 μg/ml. A: Incubation with OX26-SA-biotinfluorescein. B: Incubation with OX26 immunoliposomes loaded with carboxyfluorescein. C: Competition of cellular uptake of OX26 immunoliposomes in presence of 200 μg/ml of free OX26. Control: Background fluorescence of L6 cells. Size bars=50 μm.

Tissue sections and L6 cells of FIG. 5*b* were analysed with a Zeiss LSM 510 inverted scanning confocal microscope using 20× and 40× Zeiss Plan-Neofluor lenses with a numerical aperture of 0.5 and 1.3, respectively. A 488 nm argon laser was used in combination with fluorescein band-pass filters. Optical sections of 5.3 µm (muscle tissue) or 1.4 µm (L6 cells) were aquired and processed on a silicon graphics workstation (Silicon Graphics, Mountain View, Calif., USA) using Zeiss software. Immunofluorescence images of L6 cells were recorded with a Leica TCS NT confocal microscope (Leica) using 25× and 40× Plan Fluotar or 63× Plan Apochromat oil immersion objectives with numerical apertures of 0.75, 1.0 and 1.32, respectively.

Optical sections of 0.7–1 μm were analyzed using the Imaris software (Bitplane AG, Zurich, Switzerland) and processed using Photoshop software (Adobe Systems, Mountain View, Calif.).

REFERENCES

1. Heath, T. D., Fraley, R. T. and Papahadjopoulos, D. (1980) Antibody targeting of liposomes: cell specificity obtained by conjugation of F(ab')2 to vesicle surface. Science 210, 539–541
2. Huwyler, J., Wu, D. and Pardridge, W. M. (1996) Brain drug delivery of small molecules using immunoliposomes. Proc. Natl. Acad. Sci. USA 93, 14164–14169
3. Maruyama, K., Holmberg, E., Kennel, S. J., Klibanov, A., Torchilin, V. P. and Huang, L. (1990) Characterization of in vivo immunoliposome targeting to pulmonary endothelium. J Pharm Sci 79, 978–84
4. Emanuel, N., Kedar, E., Bolotin, E. M., Smorodinsky, N. I. and Barenholz, Y. (1996) Targeted delivery of doxorubicin via sterically stabilized immunoliposomes: pharmacokinetics and biodistribution in tumor-bearing mice. Pharm. Res. 13, 861–868
5. Allen, T. M., Brandeis, E., Hansen, C. B., Kao, G. Y. and Zalipsky, S. (1995) A new strategy for attachment of antibodies to sterically stabilized liposomes resulting in efficient targeting to cancer cells. Biochim. Biophys. Acta 1237, 99–108
6. Kirpotin, D., Park, J. W., Hong, K., Zalipsky, S., Li, W. L., Carter, P., Benz, C. C. and Papahadjopoulos, D. (1997) Sterically stabilized anti-HER2 immunoliposomes: design and targeting to human breast cancer cells in vitro. Biochemistry 36, 66–75
7. Moradpour, D., Compagnon, B., Wilson, B. E., Nicolau, C. and Wands, J. R. (1995) Specific targeting of human hepatocellular carcinoma cells by immunoliposomes in vitro. Hepatology 22, 1527–1537
8. Nassander, U. K., Steerenberg, P. A., Poppe, H., Storm, G., Poels, L. G., De, J. W. and Crommelin, D. J. (1992) In vivo targeting of OV-TL 3 immunoliposomes to ascitic ovarian carcinoma cells (OVCAR-3) in athymic nude mice. Cancer Res. 52, 646–653
9. Suzuki, S., Uno, S., Fukuda, Y., Aoki, Y., Masuko, T. and Hashimoto, Y. (1995) Cytotoxicity of anti-c-erbB-2 immunoliposomes containing doxorubicin on human cancer cells. Br. J. Cancer 72, 663–668
10. Zelphati, O., Zon, G. and Leserman, L. (1993) Inhibition of HIV-1 replication in cultured cells with antisense oligonucleotides encapsulated in immunoliposomes. Antisense Res Dev 3, 323–38
11. Zelphati, O., Degols, G., Loughrey, H., Leserman, L., Pompon, A., Puech, F., Maggio, A. F., Imbach, J. L. and Gosselin, G. (1993) Inhibition of HIV-1 replication in cultured cells with phosphorylated dideoxyuridine derivatives encapsulated in immunoliposomes. Antiviral Res 21, 181–95
12. Gagne, J. F., Desormeaux, A., Perron, S., Tremblay, M. J. and Bergeron, M. G. (2002) Targeted delivery of indinavir to HIV-1 primary reservoirs with immunoliposomes. Biochim. Biophys. Acta. 1558, 198–210
13. Dufresne, I., Desormeaux, A., Bestman-Smith, J., Gourde, P., Tremblay, M. J. and Bergeron, M. G. (1999) Targeting lymph nodes with liposomes bearing anti-HLA-DR Fab' fragments. Biochim Biophys Acta 1421, 284–94
14. Jefferies, W. A., Brandon, M. R., Williams, A. F. and Hunt, S. V. (1985) Analysis of lymphopoietic stem cells with a monoclonal antibody to the rat transferrin receptor. Immunology 54, 333–341
15. Pardridge, W. M. (1995) Vector-mediated peptide drug delivery to the brain. Adv. Drug Delivery Rev. 15, 109–146
16. Huwyler, J., Yang, J. and Pardridge, W. M. (1997) Receptor mediated delivery of daunomycin using immunoliposomes: pharmacokinetics and tissue distribution in the rat. J. Pharmacol. Exp. Ther. 282, 1541–1546
17. Frank, M. M. (1993) The reticuloendothelial system and bloodstream clearance. J. Lab. Clin. Med. 122, 487–488
18. Gregoriadis, G., Senior, J., Wolff, B. and Kirby, C. (1985) Targeting of liposomes to accessible cells in vivo. Ann. N.Y. Acad. Sci. 446, 319–340
19. Gabizon, A. and Papahadjopoulos, D. (1992) The role of surface charge and hydrophilic groups on liposome clearance in vivo. Biochim. Biophys. Acta 1103, 94–100
20. Allen, T. M. (1994) Long-circulating (sterically stabilized) liposomes for targeted drug delivery. Trends Pharmacol. Sci. 15, 215–220
21. Gabizon, A. A. (2001) Pegylated liposomal doxorubicin: metamorphosis of an old drug into a new form of chemotherapy. Cancer Invest. 19, 424–436
22. Maruyama, K., Takizawa, T., Yuda, T., Kennel, S. J., Huang, L. and Iwatsuru, M. (1995) Targetability of novel immunoliposomes modified with amphipathic poly(ethylene glycol)s conjugated at their distal terminals to monoclonal antibodies. Biochim. Biophys. Acta 1234, 74–80
23. Hansen, C. B., Kao, G. Y., Moase, E. H., Zalipsky, S. and Allen, T. M. (1995) Attachment of antibodies to sterically stabilized liposomes: evaluation, comparison and optimization of coupling procedures. Biochim. Biophys. Acta 1239, 133–144
24. Abuchowski, A., Kazo, G. M., Verhoest, C. R., Jr., Van Es, T., Kafkewitz, D., Nucci, M. L., Viau, A. T. and Davis, F. F. (1984) Cancer therapy with chemically modified enzymes. I. Antitumor properties of polyethylene glycol-asparaginase conjugates. Cancer Biochem. Biophys. 7, 175–186
25. Torchilin, V. P., Levchenko, T. S., Lukyanov, A. N., Khaw, B. A., Klibanov, A. L., Rammohan, R., Samokhin, G. P. and Whiteman, K. R. (2001) p-Nitrophenylcarbonyl-PEG-PE-liposomes: fast and simple attachment of specific ligands, including monoclonal antibodies, to distal ends of PEG chains via pnitrophenylcarbonyl groups. Biochim. Biophys. Acta 1511, 397–411
26. Bendas, G., Krause, A., Bakowsky, U., Vogel, J. and Rothe, U. (1999) Targetability of novel immunoliposomes prepared by a new antibody conjugation technique. Int. J. Pharm. 181, 79–93
27. Hermanson, G. T. (1996) Bioconjugate techniques, Academic Press, San Diego
28. Kang, Y. S. and Pardridge, W. M. (1994) Use of neutral avidin improves pharmacokinetics and brain delivery of biotin bound to an avidin-monoclonal antibody conjugate. J. Pharmacol. Exp. Ther. 269, 344–350
29. Ponka, P. and Lok, C. N. (1999) The transferrin receptor: role in health and disease. Int. J. Biochem. Cell Biol. 31, 1111–1137
30. Friden, P. M., Olson, T. S., Obar, R., Walus, L. R. and Putney, S. D. (1996) Characterization, receptor mapping and blood-brain barrier transcytosis of antibodies to the human transferrin receptor. J. Pharmacol. Exp. Ther. 278, 1491–1498
31. Yoshikawa, T. and Pardridge, W. M. (1992) Biotin delivery to brain with a covalent conjugate of avidin and a monoclonal antibody to the transferrin receptor. J. Pharmacol. Exp. Ther. 263, 897–903
32. Mandel, J. L. and Pearson, M. L. (1974) Insulin stimulates myogenesis in a rat myoblast line. Nature 251, 618–620
33. Cerletti, A., Drewe, J., Fricker, G., Eberle, A. N. and Huwyler, J. (2000) Endocytosis and transcytosis of an immunoliposome-based brain drug delivery system. J. Drug Targeting 8, 435–447
34. Laverman, P., Zalipsky, S., Oyen, W. J., Dams, E. T., Storm, G., Mullah, N., Corstens, F. H. and Boerman, O. C. (2000) Improved imaging of infections by avidin-induced clearance of 99 mTc-biotin-PEG liposomes. J. Nucl. Med. 41, 912–918
35. Wong, J. Y., Kuhl, T. L., Israelachvili, J. N., Mullah, N. and Zalipsky, S. (1997) Direct measurement of a tethered ligand-receptor interaction potential. Science 275, 820–822
36. Li, J. Y., Sugimura, K., Boado, R. J., Lee, H. J., Zhang, C., Duebel, S. and Pardridge, W. M. (1999) Genetically engineered brain drug delivery vectors: cloning, expression and in vivo application of an anti-transferrin receptor single chain antibody-streptavidin fusion gene and protein. Protein Eng. 12, 787–796
37. Morrison, S. L. and Shin, S. U. (1995) Genetically engineered antibodies and their application to brain delivery. Adv. Drug Delivery Rev. 15, 147–175
38. Lee, H. J., Zhang, Y., Zhu, C., Duff, K. and Pardridge, W. M. (2002) Imaging brain amyloid of Alzheimer disease in vivo in transgenic mice with an Abeta peptide radiopharmaceutical. J. Cereb. Blood Flow Metab. 22, 223–231
39. Ozawa, E. (1989) Transferrin as a muscle trophic factor. Rev. Physiol. Biochem. Pharmacol. 113, 89–141
40. Sorokin, L. M., Morgan, E. H. and Yeoh, G. C. (1987) Transferrin receptor numbers and transferrin and iron uptake in cultured chick muscle cells at different stages of development. J. Cell Physiol. 131, 342–353
41. Fava, R. A., Comeau, R. D. and Woodworth, R. C. (1981) Specific membrane receptors for diferric-transferrin in cultured rat skeletal myocytes and chickembryo cardiac myocytes. Biosci. Rep. 1, 377–385
42. Gosselin, M. A. and Lee, R. J. (2002) Folate receptor-targeted liposomes as vectors for therapeutic agents. Biotechnol. Annu. Rev. 8, 103–131

What is claimed is:

1. A liposome composition comprising
a) a compound of the formula

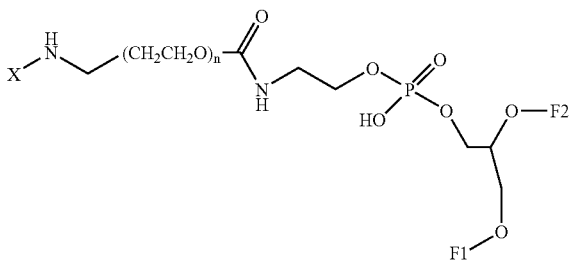

wherein n=from 14 to 85, and F1 and F2 are each independently a fatty acid chain; and b) a compound of the formula Z-Y,
wherein z is any compound capable of binding to a cellular receptor, and X and Y are compounds which interact with each other non-covalently.

2. The liposome composition of claim 1, wherein X is biotin and Y is avidin or streptavidin.

3. The liposome composition of claim 2, wherein X is biotin and Y is streptavidin.

4. The liposome composition of claim 1, wherein n=from 28 to 50.

5. The liposome composition of claim 1, wherein F1 and F2 are each stearic acid.

6. The liposome of claim 1, wherein Z is an antibody.

7. A method for producing a liposome composition comprising
a. conjugating a compound Z with compound Y; and
b. mixing the product of a) with a compound of the formula

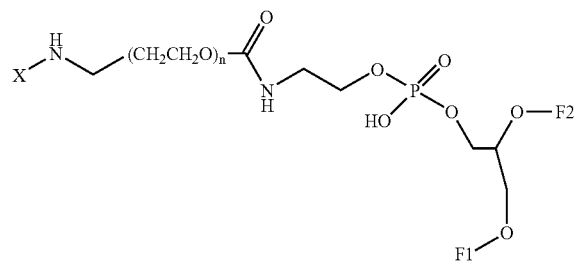

wherein n=from 14 to 85, F1 and F2 are each independently a fatty acid chain, Z is a compound capable of binding to a cellular receptor, and X and Y interact with each other non-covalently.

8. The method of claim 7, wherein X is biotin and Y is avidin or streptavidin.

9. The method of claim 8, wherein X is biotin and Y is streptavidin.

10. The method of claim 7, wherein n=from 28 to 50.

11. The method of claim 7, wherein F1 and F2 are each stearic acid.

12. The method of claim 7, wherein Z is an antibody.

13. An immunoliposome, comprising distearoylphosphatidylcholine and a compound of the formula

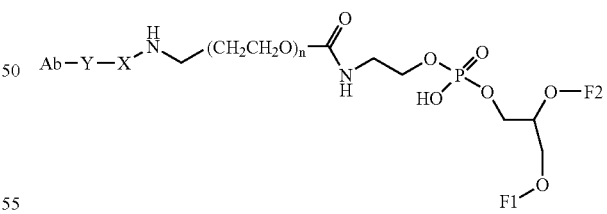

wherein n=from 14 to 85, F1 and F2 are each independently a fatty acid chain, Ab is an antibody capable of binding to a cellular receptor antigen, and X and Y are compounds which are non-covalently bound to each other.

14. The immunoliposome of claim 13, wherein X is biotin and Y is avidin or streptavidin.

15. The immunoliposome of claim 13, wherein Ab is an OX26 monoclonal antibody against the transferrin receptor.

* * * * *